United States Patent [19]

Chernajovsky

[11] Patent Number: 5,723,332
[45] Date of Patent: Mar. 3, 1998

US005723332A

[54] TRANSLATIONAL ENHANCER DNA

[75] Inventor: Yuti Luis Alberto Chernajovsky, London, England

[73] Assignee: British Technology Group Limited, London, England

[21] Appl. No.: 633,779

[22] PCT Filed: Nov. 25, 1994

[86] PCT No.: PCT/GB94/02586

§ 371 Date: Apr. 19, 1996

§ 102(e) Date: Apr. 19, 1996

[87] PCT Pub. No.: WO95/14775

PCT Pub. Date: Jun. 1, 1995

[30] Foreign Application Priority Data

Nov. 26, 1993 [GB] United Kingdom .................. 9324394
Sep. 1, 1994 [GB] United Kingdom .................. 9417597

[51] Int. Cl.$^6$ .................................................. C07H 21/04
[52] U.S. Cl. .................... 435/320.1; 536/23.1; 536/24.1
[58] Field of Search .................. 435/69.1, 320.1; 536/23.1, 23.2, 24.1

[56] References Cited

U.S. PATENT DOCUMENTS 4,937,190   6/1990   Palmenberg et al. .................. 435/69.1

FOREIGN PATENT DOCUMENTS

WO 93/03143   2/1993   WIPO .

OTHER PUBLICATIONS

J.L. Cyr et al. "Molecular genetics of kinesin light chains: Generation of isoform . . . " Proceedings of the Natl Acad. Of Sci. Of the USA, Nov. 15, 1991, vol. 88 No. 22, pp. 10114–10118.

Wedaman, K., et al., J. Mol. Biol., vol.231, pp. 155–158, 1993.

Invirtogen Catalog, especially pp. 24, 27, and 29, 1991.

*Primary Examiner*—James Ketter
*Assistant Examiner*—Irem Yucel
*Attorney, Agent, or Firm*—Nixon & Vanderhye

[57] ABSTRACT

The gene which expresses the light (β-)chain of kinesin contains at its 5'-end a region of DNA of high secondary structure which provides a strong enhancer of translation. In the human kinesin gene it forms a double hairpin loop. The secondary structure, optionally with flanking sequence, is claimed as isolated DNA. Constructs in which it serves is an enhancer for expression of foreign DNA are also claimed.

8 Claims, 7 Drawing Sheets

```
                                                                        -249
CCTGCCCCGA GAGCCCCACC CCCGTCCGCG TTACAACCGG AAGGCCGCTG

-199
GGTCCTGCAC CGTCACCCTC CTCCCTGTGA CCGCCCACCT GACACCCAAA

-149
CAACTTTCTC GCCCCTCCAG TCCCCAGCTC GCCGAGCGCT TGCGGGGAGC

-99
CACCCAGCCT CAGTTTCCCC AGCCCCGGGC GGGGCGAGGG GCGATGACGT
                                 SmaI

-49
CATGCCGGCG CGCGGCATTG TGGGGCGGGG CGAGGCGGGG CGCCGGGGGG

+1
AGCAACACTG AGACGCCATT TCGGCGGCCG GGACGGGCGC AAGGCGGCCG

52
AGCGGGACTG GCTGGGTCGG CTGGGCTGCT GGTGGAGGAG CCGCGGGGCT

102
GTGCTCGGCG GCCAAGGGGA CAGCGCGTGG GTGGCCGAGG ATGCTGCGGG

├──→ hairpin loop region                   152
GCGGTAGCTC CGGCGCCCCT CGCTGGTGAC TGCTGCGCCG TGCCTCACAC

202
AGCCGAGGCG GGCTCGGCGC ACAGTCGCTG CTCCGCGCGC GCGCCCGGCG

252
GCGCTCCAGG TGCTGACAGC GCGAGAGAGC GCGGCCCTCA GGAGCAAGGC

←|                                                                       302
G GTGAGTCCC CGCGTCGTCG CCCCGGACCG CGGCCCCCTC CTCATCCTCC

352
GCCCCGTCCC TGTCCCGCTC CTCTTCGGAC CCGCCCCGGC CGCAACTCTG

402
TCCCCATCCA GGCCTCCTTC CCGGTTTGGT CCCGGCCCCT CTCCGTTCCC

452
ACCCCGGTAC CGCCCCAGT TCACCGCCCC GGCCGGTCCG CGACCCCTTC
     Asp 718
                                                                         502
TAGGTTCAGG TCGGGTTCTT GTCCCCGGCC CTTTTGCCAG CCCCGGCTCC

540
CGGCGCCGCG CGTCCTCCCC ATCCGCGTCC CACTGCAG
                                        PstI
```

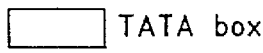 TATA box   SP1   CREB

Fig.2

```
                Met Leu Arg Gly Gly Ser Ser Gly Ala Pro Arg Trp stop
81
human  GGGTGGCCGAGG ATG CTG CGG GGC GGT AGC TCC GGC GCC CCT CGC TGG TGA
rat    GTCGGGGTGAGG ATG CTG CGG GGC GGC GGA GGC GTC GCT TGC TGC TGA
                Met Leu Arg Gly Gly Gly Val Ala Cys Cys stop
3

256
                    Met Tyr
141
human  CTGCTGCGC........ATG TAT.........
rat    GGCGGGCTGG........ATG CAT.........
                         Met His
62                       121

Fig.3
```

TRANSLATIONAL ENHANCER DNA

BACKGROUND OF THE INVENTION

1. Field of the Invention

The invention relates to DNA useful as an enhancer of translation of nucleic acids in the production of proteins therefrom.

2. Description of the Related Art

Kinesins are molecular motor proteins implicated in the intracellular transport of organelles in brain cells and in the movement of chromosomes along microtubules during cell division. In sea urchin and mammalian cells, kinesins have been characterized as tetrameric proteins. Two subunits are the two heavy chains (α chains) of a relative molecular mass of approximately 120 kDa and two light chains (β chains) of approximately 70 kDa. Intracellular organelles move along microtubules inside the cell by attaching to the tetrameric αα/ββ kinesin molecular motor. The α chains provide the tubulin binding site and the ATPase domain, whereas the β chains are responsible for the specific attachment of the organelle to be moved by the kinesin tetramer.

At present three rat brain kinesin β chain cDNAs have been cloned, (J. L. Cyr et al., Proc. Natl. Acad. Sci. USA 88, 10114–10118) and a partial cDNA sequence (named EST00761) of human brain origin has been entered on the EMBL database as a result of the human genome sequencing work reported by M. D. Adams et al., (Nature 355, 632–634 (1992)). The three rat cDNAs are the product of one gene spliced differentially at the 3'-end, producing different COOH terminal ends in the protein and thereby predicting three different isoforms of β-light chain, designated "A", "B" and "C". This mechanism seems to confer the kinesin specificity for organelle binding.

A human β-kinesin cDNA sequence of length 2309 bp has been entered on the EMBL database under Accession No. L04733 by L. B. Lachman et al. and published as Cabeza-Arveliz et al., DNA Cell Biol. 12, 881–892, 1993.

SUMMARY OF THE INVENTION

It has now been found that the β-chain kinesin genomic DNA contains a region of DNA of high secondary structure which provides a strong enhancer of translation (not to be confused with an enhancer of promotion). In the human kinesin, the secondary structure lies within the first exon of the gene, which provides the 5'-untranslated end of the mRNA. It takes the form of a double hairpin loop which is illustrated for the mRNA in FIG. 4 of the drawings and listed in the sequence listing as SEQ ID NO:6.

The invention includes isolated DNA from part of the β-light chain gene of a kinesin as well as various constructs in which this DNA serves as a translational enhancer. Thus, in one aspect, it includes isolated DNA from the 5'-end of the allelic gene which expresses the β-light chain of a kinesin, said DNA being a translational enhancer and comprising a region of high secondary structure, capable of being represented as a hairpin loop; or a translation-enhancing substitution or deletion mutant thereof.

The isolated DNA thus includes the secondary structure region and optionally additional DNA to the 5'- or 3'-end thereof, which may be the DNA native to the same kinesin gene. Thus, the isolated DNA can include any or all such DNA extending in the 5'-direction back to the 5'-end of the β-light chain gene. Thus, it may include part or all of the promoter region which extends upstream of the mRNA start site. It may include part or all of the first intron (which lies between the first exon coding for untranslated mRNA and the second exon coding for the N-terminal region of the β-kinesin protein).

Since the β-kinesin promoter is not particularly strong, the invention can be put to better use by linking the translational enhancer DNA to a strong eukaryotic promoter. Thus, in another aspect the invention provides a construct for enhanced expression of non-β-kinesin DNA encoding a protein, comprising (1) a eukaryotic promoter, which is preferably a foreign promoter stronger than that of the native β-kinesin gene, (2) downstream thereof, translational enhancer DNA of the invention and (3), downstream of the enhancer, foreign DNA i.e. coding for a protein other than β-kinesin.

The β-kinesin gene also contains within the first exon, upstream of the secondary structure, a region which codes for a small protein (12 aa long). This region appears designed to facilitate the binding of a ribosome to the mRNA somewhat downstream thereof. Accordingly, the first exon of the β-kinesin gene appears to provide an internal entry ribosome site (IRES). Such a site enables the mRNA to be translated independently of any translation initiation sites. Effectively it can provide a way of enabling two genes to be transcribed using a single promoter. Thus, in another aspect the invention provides a construct for expression of two protein-coding DNAs which comprises (1) a eukaryotic promoter, (2) downstream of the promoter, first foreign DNA, i.e. DNA coding for a first protein other than β-kinesin and which lacks a termination of transcription signal, (3) downstream of the first foreign DNA, DNA of the invention, further comprising the small protein-coding region, thus serving as an internal ribosome entry site (IRES) and for enhancement of translation and (4) downstream of the IRES-translational enhancer DNA, second foreign DNA, i.e. DNA coding for a second protein other than β-kinesin and which is distanced downstream from the IRES-translational enhancer DNA so as to permit translation of mRNA from the IRES.

BRIEF DESCRIPTION OF THE DRAWINGS

FIG. 2 shows the DNA sequence of a 838 kb length of DNA at the 5'-end of the human β-kinesin gene, which is the same sequence as in SEQ ID NO:1 but with a graphic depiction of features;

FIG. 3 shows a DNA sequence comparison of human kinesin and rat cDNAs including a sequence corresponding to part of the first exon of the human genomic DNA which codes for a 12aa peptide (these sequences are the same sequences as in SEQ ID NO:2 and SEQ ID NO:3 (human sequences) and SEQ ID NO:4 and SEQ ID NO:5(rat sequences)) and further including the beginning of the coding sequence;

DESCRIPTION OF THE PREFERRED EMBODIMENTS

FIG. 2 corresponding to SEQ ID NO:1 shows the DNA sequence (838 nucleotides) of the 5' flanking, exon and intron of the human β-kinesin gene. Numbers indicate position of the nucleotide after the initiation site of transcription of mRNA (+1) or upstream of it (negative numbers). The first exon, from 1 to 253, is in italics and underlined. Restriction enzyme sites are underlined and indicated. Putative TATA box, SP1 and cAMP-modulated transcription factor (CREB) binding sites are in shaded areas.

As will be seen, the promoter region runs from nucleotide −1 to at least −121 as shown by the identified transcription factor binding sites normally present in eukaryotic promoters. At the other end of the sequence, nucleotides 254 onwards are part of a first intron region thought to be more than 9 kb long.

Figure 4:
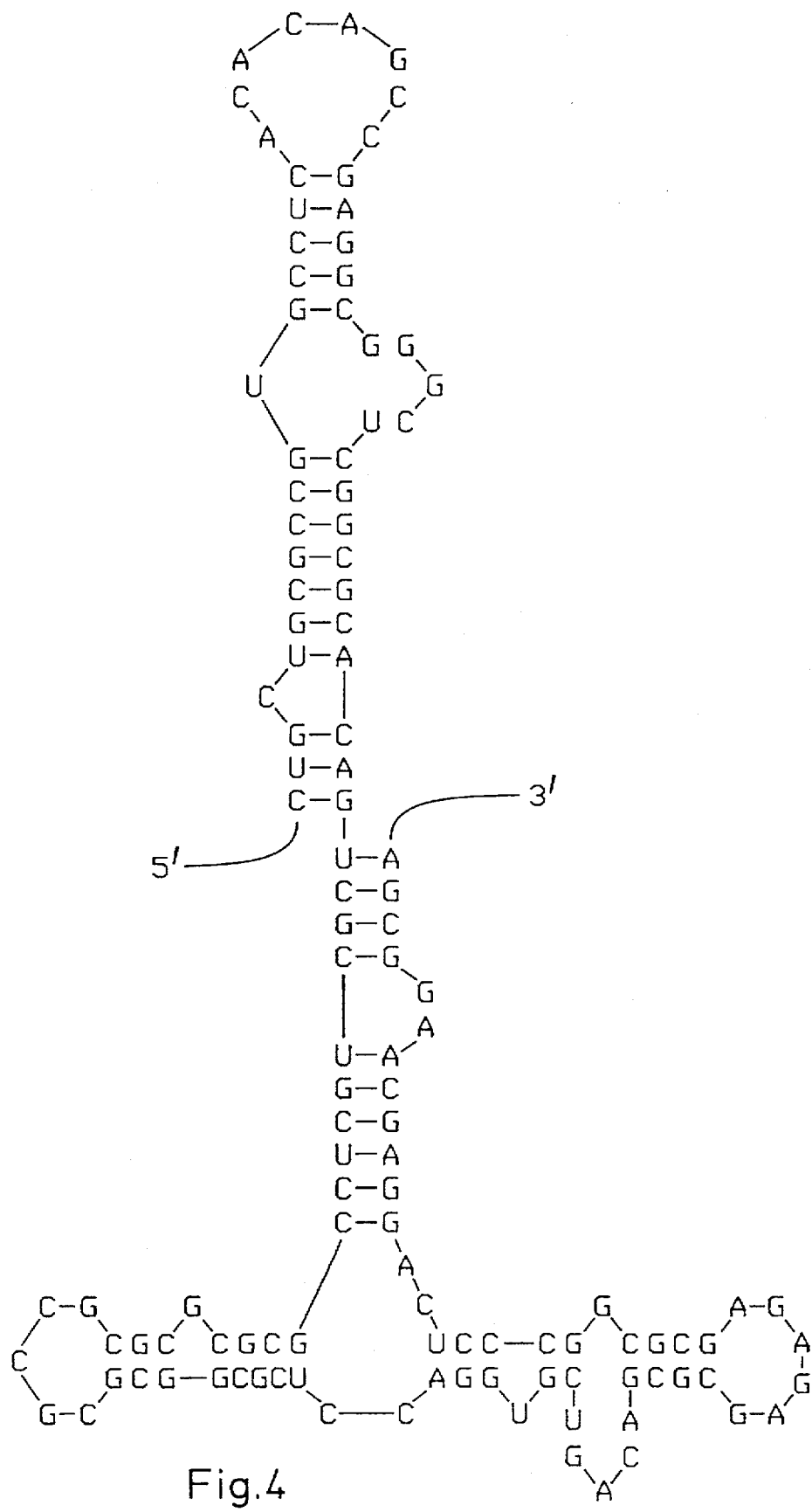
FIG. 4 shows a region of high secondary structure (translational enhancer) within the human kinesin mRNA corresponding to another part of the first exon of the genomic DNA corresponding to SEQ ID NO:6.

FIG. 4 corresponding to SEQ ID NO:6 indicates the high degree of secondary structure responsible for the enhancer function of a DNA of the invention which comes from the human β-kinesin gone. The Figure is drawn up in terms of mRNA bases, but is readily transposable to genomic or cDNA by substituting thymines (T) for uracils (U) throughout. Thus, the left-hand end of the mRNA beginning CUGCUG ... transposes to nucleotides CTGCTG ... at 132 to 137 in FIG. 2, while the right-hand end of the mRNA ending ... AGGCG(A) is present at nucleotides 249–253 of FIG. 2. The A nucleotide at the end of the RNA is that of the putative start codon at the beginning of the second exon and therefore does not appear in FIG. 2.

The translational enhancer region shown has a potential double hairpin loop, one straight loop extending from the 5'-end, from nucleotide 132 to 176 and the second a branched loop, from nucleotides 177 to 253. This second loop is therefore 76 nucleotides long. Since, however, the rat β-kinesin cDNA sequence is 67 nucleotides shorter than the human within the region of the second loop, it may reasonably be assumed that most of the 76-long second loop is missing in the rat DNA. Since, further, the β-kinesin gene is well expressed in rats, the reasonable probability is that only the first loop is necessary for translational enhancement. Thus, it is believed that the core area of high secondary structure necessary for a translational enhancer is that of the first loop referred to.

It will be appreciated that the area of high secondary structure for β-kinesin will differ somewhat from one creature to another and that the invention includes sufficient of the area to act as a translational enhancer regardless from which mammal, animal or other being it is derived or to which it approximates.

Excessive lengths of enhancer can be trimmed back if desired, e.g. using the Bal31 enzyme or the polymerase chain reaction could be used to generate any desired shorter length. Additional lengths of DNA, whether native to β-kinesin or not, can be added to the 3'- or 5'-end. Preferably native DNA comprises from 1 to 100 base pairs of 5'- or 3'-flanking genomic DNA.

It will be appreciated that the secondary structure can be altered in minor respects by substitution of DNA bases, especially in those regions which are not self-paired and especially in those regions which are not self-paired and especially in the downstream (3'-part) of the first hairpin loop and anywhere within the second hairpin loop. Especially, up to 10% of the DNA bases in the loop may be varied and a few deletions, typically not more than four, may alternatively or additionally be made. Such mutations must not be so drastic as to affect the enhancer function.

The β-kinesin mRNA contains a short open-reading frame that is conserved between rat and man: see FIG. 3. This open reading frame does not contain upstream a consensus ribosomal binding site. It is thought that such short open reading frame is of advantage to help the ribosome slide to a stronger internal consensus ribosomal site, because the first AUG codon lies in an unfavourable context for initiation. This ORF is believed useful to impart to the region an internal ribosome entry site (IRES)function. IRES functions have been found in other genes, but mainly in viruses, e.g. HIV, EMCV or poliovirus, and are regarded as rare in animal genes.

Incidentally, the human β-kinesin sequence in FIG. 3 differs from that of the corresponding cDNA sequence in the EMBL database by having a cytidine (C) residue at position 124, instead of an adenine (A).

In the constructs of the invention the β-kinesin promoter is preferably replaced or preceded by a stronger eukaryotic promoter such as from Epstein-Barr Virus, SV40, a long terminal repeat (LTR) of a retrovirus or a cytomelagovirus (CMV) or it may be an inducible promoter such as metallothionein.

The distances between promoter and enhancer (on the 5'-side of the enhancer) and enhancer and start codon of the foreign gene (on the 3'-side of the enhancer) are believed not to be critical to the invention. The same goes for distances between promoter and start codon of the first foreign gene and between enhancer and start codon of the second foreign gene, in the case of the IRES constructs of the invention. Indeed, on the 3'-side of the enhancer, the first intron region in the β-kinesin gene has a length of about 9 kilobase pairs, so separations of up to 9 kbp at least are likely to be operable. In the Examples, the distance is about 150 bp. Simple further experiment to determine the precise minimum distance is easily accomplished by the person skilled in the art.

Any foreign genes can be used in the constructs of this invention but proteins composed of two polypeptide subunits (such as antibodies) are of particular interest to be used in the IRES constructs due to the efficiency of expression from a single promoter and one mRNA molecule.

The following Examples illustrate the invention. All plasmids referred to were cloned and maintained in *E. coli* DH5a cells, a well known strain. Nucleotide nomenclature is that of FIG. 2.

EXAMPLE 1

A human placental genomic DNA library, obtained from Clontech, was cloned in the λ EMBL3 phage vector. Thirty plates (15 cm in diameter) were plated with 20,000 phages each. After transfer to nylon membranes and crosslinking with u.v. light the filters were probed with the full length cDNA (2.4 kb) of human kinesin light chain labelled by random priming with calf thymus DNA primers. Salmon sperm and *E. coli* DNA (at 50 mg/ml each) were used during the prehybridization and hybridization steps. In the first screen, 33 plaques were isolated, from which 11 were true positives and reached the third screening and purification step. These clones were separated into ten groups based on their different restriction fragment patterns with EcoRI and XhoI. The results indicate that the introns of the kinesin gene are large, suggesting that the gene spans more than 90 kb.

Figure 1:
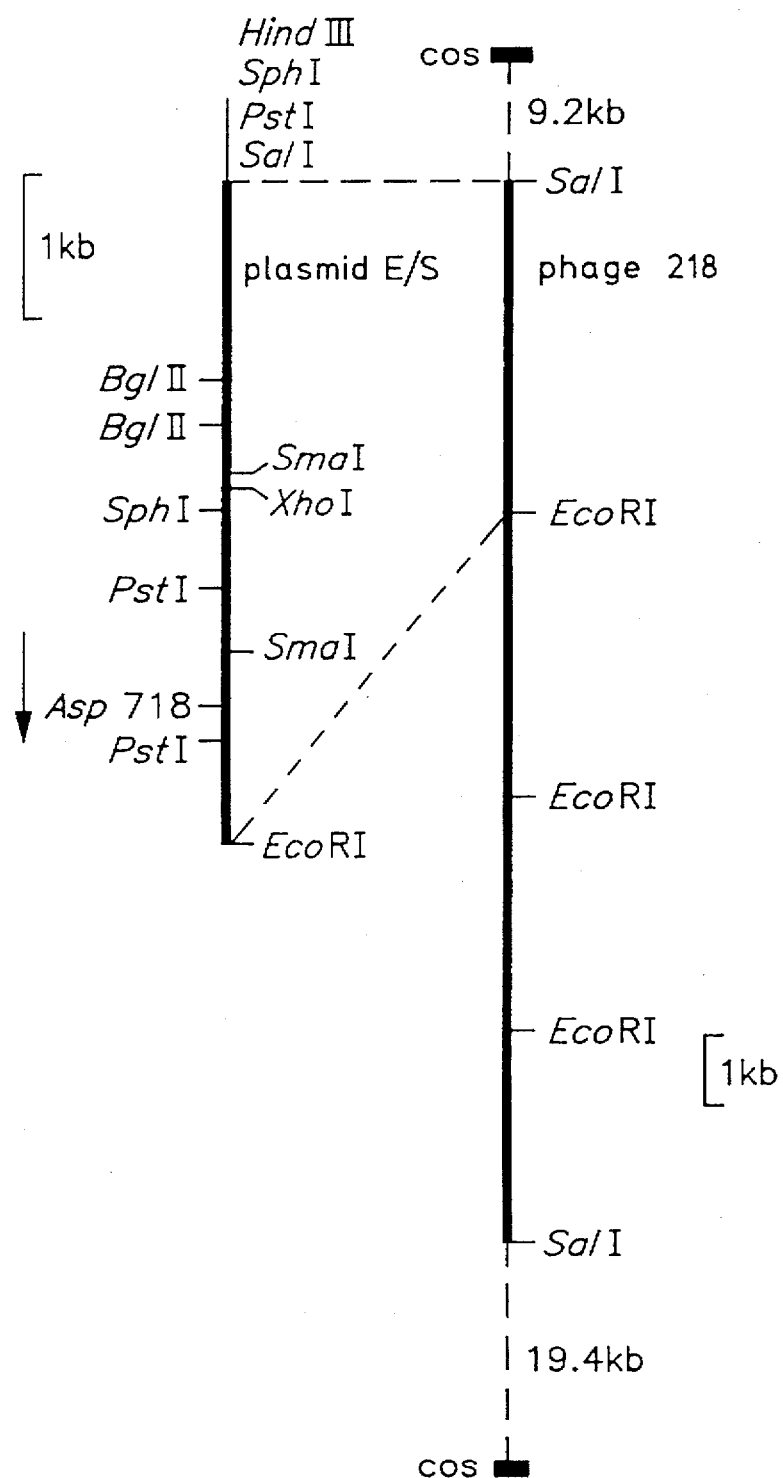
FIG. 1 is a restriction enzyme map of a phage 2.1B isolated from genomic DNA of human β-kinesin and of a cloned fragment thereof inserted in a plasmid E/S.

A human kinesin β-chain cDNA (EMBL database accession number LO4733) from a T cell library, named βi-kinesin (i=originating from an immune cell) in pGem3Z was kindly provided by Dr. L. B. Lachman (Dept. of Cell Biology, M. D. Anderson Cancer Center, Houston, Tex., U.S.A. A 5' HindIII fragment of the cDNA (0.3 kb) was used as a probe and showed strong hybridisation to three groups of clones. One of these clones, 2.1B, was selected for further work. Its restriction map is shown in FIG. 1 (top). "Cos" denote the cohesive ends of the phage. The 4.6 EcoRI- SalI fragment, a restriction map of which is shown in FIG. 1 (bottom) wherein the arrow represents the sequence of FIG. 2, was further subcloned into plasmid pUC19. The resultant plasmid, denoted "E/S", was sequenced by dideoxy sequencing using T7 DNA polymerase ("Sequenase", USB). Smaller fragments, that hybridized with the 0.3 kb 5' end of the cDNA, were also subcloned. These were a 1.2 kb PstI and a 0.6 kb PstI-SmaI- fragment. The full DNA sequence of the PstI-SmaI (0.6 kb) fragment and additional sequence of the 5' genomic flanking sequence are shown in SEQ. ID. NO:1 and FIG. 2. These sequences encompass the promoter area, and the first exon together with part of the first intron of the β-kinesin gene.

The promoter sequence contains several putative transcription factor binding sites including SP1 (GGCGGGG) at nucleotides −121 to −115, −75 to −69 and −65 to −59. CREB (ATGACGTCA) at nucleotides −46 to −37 and TATA box (CATTTC) at nucleotides −32 to −27 as shown in FIG. 2. The first exon is 253 nucleotides long and corresponds to the 5'- untranslated region of the mRNA. Comparison of this DNA region with the recently cloned rat cDNAs showed, as expected, evolutionary divergence at this area, but surprisingly also showed a high degree of homology in an area at nucleotides 93–131 with potential for encoding a small peptide, 12 amino acids long in humans SEQ ID NO:3, and 12 amino acids long in rat kinesin light chain isoforms A and C SEQ ID NO:5, that is not preceded by a consensus ribosomal binding site (FIG. 3). (Note: in this part of the rat cDNA the A and C predicted isoforms are believed identical with the B). This coding region is followed immediately by a GC-rich region capable of forming very stable secondary mRNA structure (AG=−52.2 kcal/mol) as shown in FIG. 4. Interestingly only the human mRNA could form a double hairpin structure that requires 122 nucleotides (Nos. 132–253), while the rat mRNA has only 67 nucleotides in this region, before the kinesin protein start site, and its potential single hairpin structure has lower stability (AG=−23.8 kcal/mol).

Figure 5:
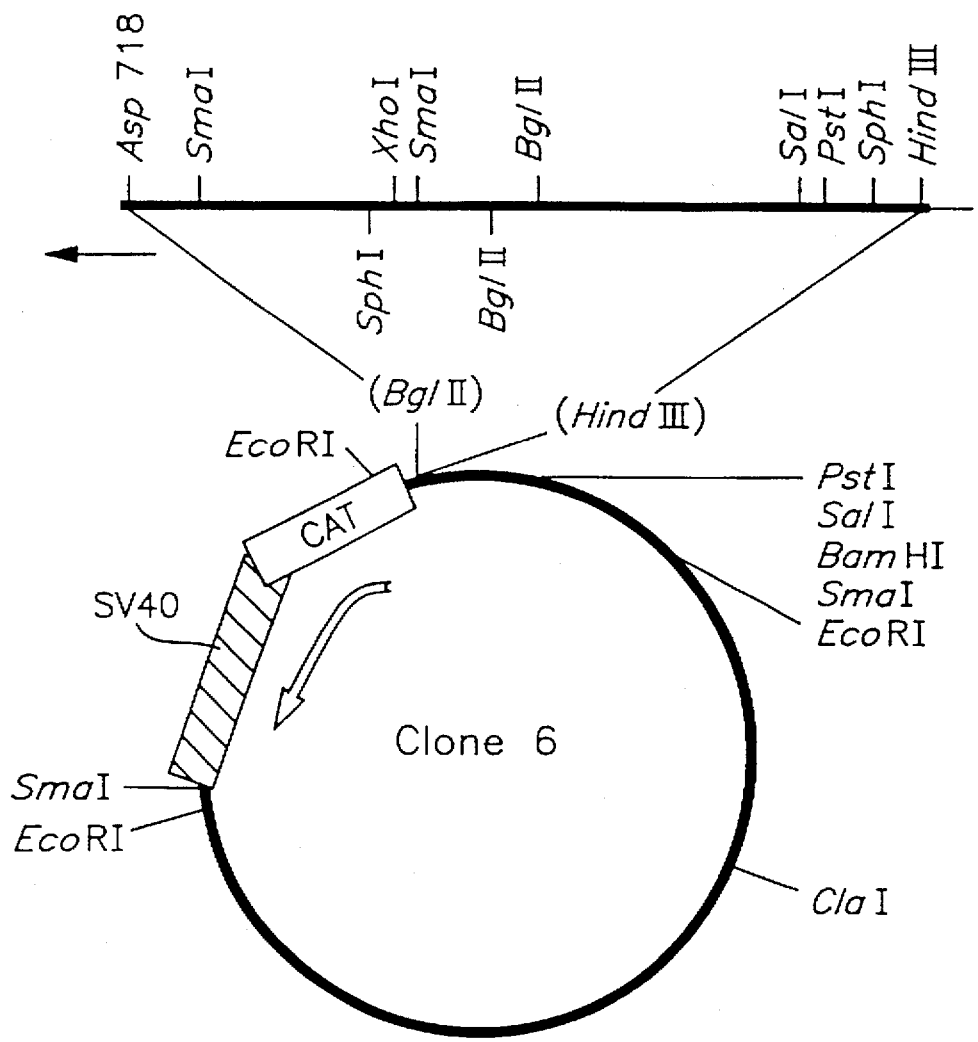
FIG. 5 shows the insertion of a portion of the sequence of FIG. 2 including the enhancer into a plasmid containing a CAT reporter gene.
Figure 6:
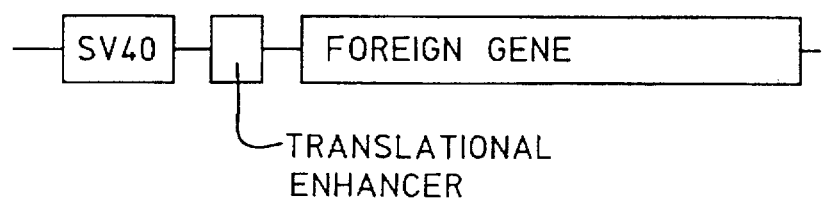
FIGS. 6 and 7 show schematically two DNA constructs incorporating the translational enhancer DNA of the invention.
Figure 7:
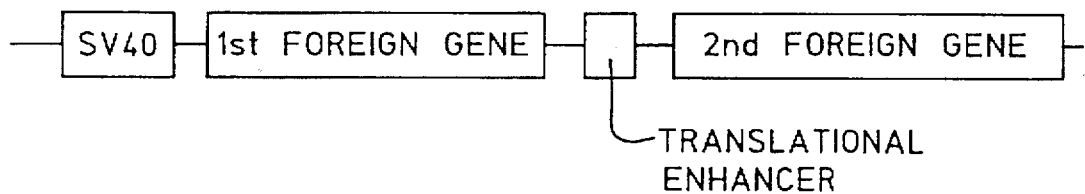

In order to show that the region of genomic DNA cloned and sequenced is functional, a reporter plasmid in which the β-kinesin promoter drives transcription of the bacterial chloramphenicol acetyltransferase gene, was constructed as follows. The HSV-tk promoter was removed from the vector pBLCAT9+, L. Klein-Hitpass et al., Nucleic Acids Research 16, 647–663 (1988), using HindIII and BglII and these ends were blunted with Klenow fragment of DNA polymerase and filled in with dNTPs. The HindIII to Asp718 3.6 kb fragment from the kinesin promoter region was similarly blunted and filled-in and ligated to the CAT gene in this vector with only a small intervening amount of sequence before the CAT gene start codon. The orientation of the insert in relation to the CAT gene was assessed by restriction with BamHI and BglII. The plasmid containing the promoter in the right orientation regarding the CAT gene was named "clone 6". FIG. 5 shows the resulting plasmid which has the SV40 polyadenylation signal following the CAT gene and also contains an ampicillin resistance marker gene (not shown). "Clone 6" was co-transfected with the selectable marker plasmid pSV2neo into HeLa cells. As a control, the plasmid pBLCAT9+, that has the HSV thymidine kinase (HSV-tk) promoter driving the same bacterial reporter gene, was also co-transfected with pSV2neo. The cells were co-transfected by the calcium phosphate precipitation method with 20 mg of reporter (CAT) gene plasmid and 1 mg of selectable plasmid. After transfection, cells were osmotically shocked with 10% glycerol in DMEM for 4 minutes, washed twice with DMEM serum-free medium, allowed to recover for 48 hours in DMEM with 10% FBS and then trypsinized and diluted 1 to 4 into media containing 1 mg/ml G418. After two to three weeks. 30–40 clones were pooled and grown as a single population of cells. CAT assays were performed as described previously, Y. Chernajovsky et al., Lymphokine Research 9, 199–212 (1990) and C. M. Gorman et al., Molecular and Cellular Biology 2, 1044–1051 (1982), The expression of the CAT gene from the β-kinesin cDNA fragment in the reporter gene plasmid was constitutive, as was the expression from the HSV-tk promoter in the control plasmid. The percentage conversion of chloramphenicol to its acetylated derivative was measured under conditions which gave a linear dependence of conversion on the enzyme concentration. Calibration of the amount of protein extract necessary to obtain a linear CAT assay, showed that cells transfected with "clone 6" gave about the same conversion from 0.2 μg protein of CAT activity from "clone 6" as from 15 μg protein of the control plasmid. This represents 75-fold more CAT activity per unit weight of protein extract than extracts from the pBLCAT9+ transfected cells.

Attempts were made to upregulate the kinesin promoter with second messenger analogs of the cAMP kinase signalling pathway, or protein kinase C. Cholera toxin, forskolin and PMA failed to induce the expression of the reporter genes. On the contrary, they were slightly inhibitory to the β-kinesin promoter and strongly inhibitory for the control (HSV-tk promoter driven) plasmid.

EXAMPLE 2

Similar experiments were performed with human lung fibroblasts and the expression of β-kinesin mRNA measured by Northern blot. No changes in expression were seen after treatment with PMA, dibutyryl cAMP or double stranded RNA.

EXAMPLE 3

Example 1 was repeated but using the neuroblastoma cell line NB 100 obtained from Dr Audrey Evans, Director of Oncology, Children's Hospital, Philadelphia USA. The results were very similar to those of Example 1, with an approximately 75-fold increase in CAT gene expression.

EXAMPLE 4

Example 3 was repeated, substituting NSE (neuron specific enolase) promoter for the HSV-tk promoter of the control plasmid. NSE is a very strong promoter in neuroblastoma cells. Nevertheless, the construct of the invention gave a 75–100 fold increase in expression of the CAT gene.

EXAMPLE 5

This Example shows that the hairpin loop region is responsible for the translational enhancing function of the kinesin DNA of the invention.

The cDNA of kinesin βi was digested at the unique restriction sites NarI (recognising GGCGCC) and SauI (also known as AocI, recognising CTCAGG) at positions 114–119 and 239–244 of FIG. 2, respectively in order to remove the hairpin loop structure. (The hairpin structure lies between positions 133 and 255, but it is not necessary to remove the whole of it in order to destroy the self-annealing potential of the RNA). The fragment lacking the hairpin loop region was gel-purified. Its protruding ends were filled in with Klenow fragment of DNA polymerase and dNTPs and religated with T4 DNA ligase.

Plasmids pGEM3z carrying separately (a) the full length β kinesin cDNA having the hairpin loop excised, were prepared and linearized at the ApaI site located 3' of the translational stop codon.

Capped cRNA was synthesized using T7 RNA polymerase in the presence of the cap analogue 7-methyl GpppG. This cRNA was translated in vitro using a rabbit reticulocyte lysate preparation (Promega Corporation, Madison, Wisc., U.S.A.) and $^{35}$[S]-methionine, under the conditions recommended by the supplier. After translation, the products were separated on SDS-polyacrylamide gel by the Laemmli method. Gel analysis was performed by treating the gel with 1 M sodium salicylate, drying it and subjecting it to autoradiography.

Figure 8:
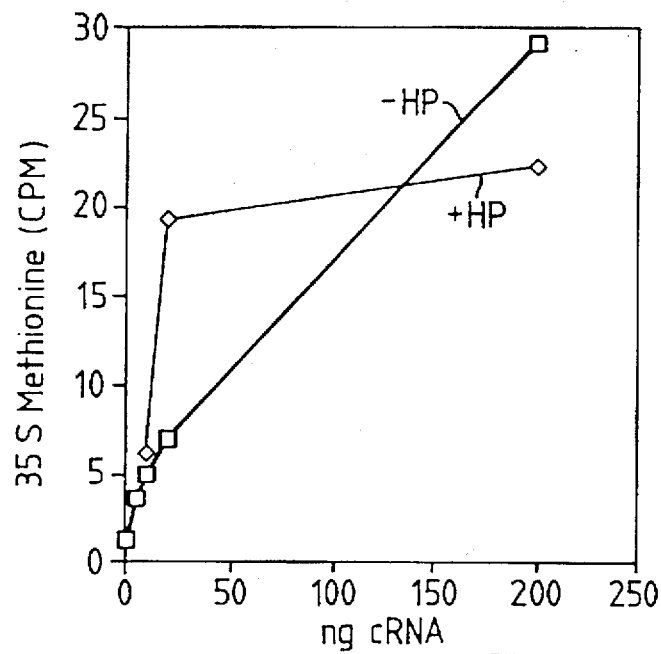
FIG. 8 shows plots of radiolabelled protein translated in vitro from human β-kinesin cRNA in a rabbit recticulocyte lysate assay.

Using dilutions of the cRNA, the efficiency of the cDNAs translation in vitro in rabbit reticulocyte lysate was compared. In FIG. 8, $^{35}$S methionine (counts per minute) is plotted on the y-axis against ng cRNA in 25 μl volume of translation medium on the x-axis. FIG. 8 shows that the cRNA without the hairpin loop structure (HP−), represented by the solid line, is less efficient in translation than cRNA from the full length original cDNA (FL), represented by the broken line. The FL cRNA gave a higher translation rate at low mRNA concentrations.

EXAMPLE 6

This Example shows that the hairpin loop region upregulates gene expression in a eukaryotic, transient expression system. This plasmid places the hairpin sequence directly 3' of a 5'-non coding region of a herpes simplex virus (HSV) thymidine kinase (tk) mRNA and includes a HSV-tk promoter which drives a CAT reporter gene. A control plasmid, pBLCAT 9, see Example 1, in which the construct is identical except that the said hairpin loop structure is missing was used for comparison.

A 150 bp, NarI-SauI gel-purified fragment, obtained as in Example 5, from the plasmid pSV2MAF, encoding the 5'-human β-kinesin UTR hairpin loop fragment was blunt-ended with Klenow fragment and ligated into SmaI-linearized pUC 18. The resultant plasmid was termed pUC18/HP.

The next step was to remove the HSV tk promoter from pBLCAT 9 plasmid, ligate it to the β-kinesin hairpin loop fragment and then insert this construct into the pBLCAT 9 vector in place of the promoter alone. The tk DNA used is 250 bp long and contains 200 bases of promoter of the 5'-non-coding region followed by 50 bases downstream of the mRNA transcription site. (HSV tk has a promoter region 200 bases long and is followed by 110 bases of DNA which is transcribed into RNA preceding the start codon of the tk gene. In this work, the last 60 bases of the 5'-non-coding DNA were not used). A 250 bp BglII-SalI, gel-purified fragment from the plasmid pBLCAT 9 encoding the tk promoter was blunt ended with Klenow fragment and ligated into Asp718-linearized, Klenow fragment-treated pUC 18/HP, so that the β-kinesin hairpin loop fragment was introduced directly 3'-containing of the HSV tk promoter DNA. This construct was termed pUC 18/Tk/HP. A 375 bp gel-purified BamHI-HindIII fragment from pUC 18/Tk/HP encoding the hairpin loop fragment and tk promoter was ligated into BamHI-HindIII cut, gel-purified pBLCAT 9. This construct was termed pBLCAT/HP and contains the following linear arrangement of DNA (5' to 3'): tk promoter—kinesin HP loop—CAT gene—SV40. The control plasmid pBLCAT 9 has the linear arrangement: tk promoter—CAT—SV40.

Figure 9:
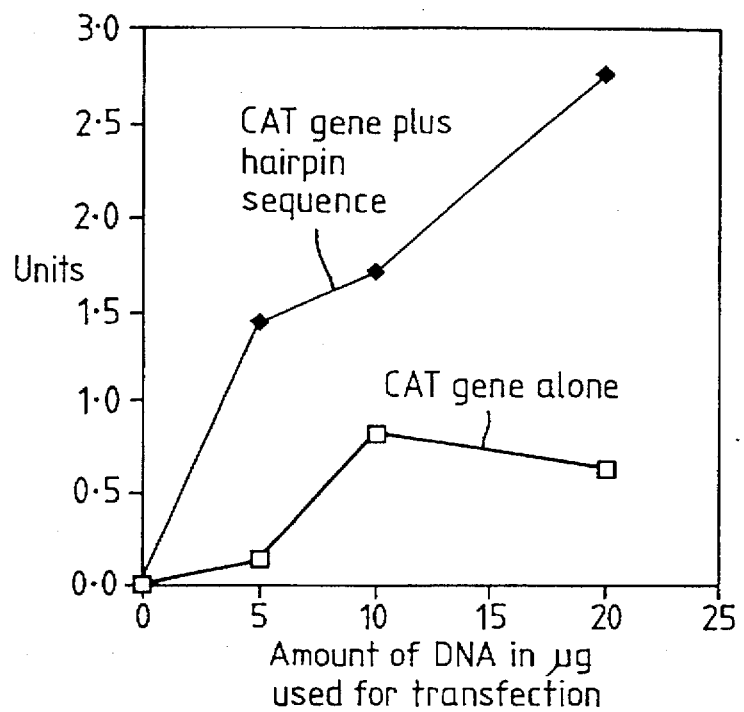
FIG. 9 shows plots of CAT activity against amounts of DNA transfected winto COS cells when the CAT gene is expressed from two plasmids differing only in that one has a human β-kinesin hairpin loop fragment between the promoter and the CAT gene.

Transient transfection of COS cells (monkey kidney fibroblasts expressing the SV40 T-antigen gene: see P. Mellon et al., Cell 27, 279–288 [1981]) by the calcium phosphate precipitation method showed that the 5' kinesin UTR hairpin loop fragment (filled squares) upregulates the expression of the CAT reporter gene by up to fourfold greater than that from a control plasmid without the hairpin loop insert (open squares). The results are shown in FIG. 9, in which units of CAT activity are plotted on the y-axis against amounts of DNA (μg) used for the transfection on the x-axis. The units of CAT activity were calculated from autoradiograms of standard thin layer chromatography assays of CAT activity and normalised to firefly luciferase activity from the plasmid pSV$_2$L, (de Wet et al. Molecular and Cellular Biology, 7, 725–737 [1987]) used at a constant 5 μg per transfection. pUC 18 DNA at 10 and 15 μg per transfection was used to maintain the total DNA for each transfection at 25 μg.

EXAMPLE 7

This Example confirms that the 5' UTR of the human kinesin gene acts as an IRES. A polycistronic retroviral vector SR10 was constructed and described as follows:

A PCR fragment of about 185 bp containing the hairpin region of the human kinesin gene was amplified from the plasmid pSV$_2$MAF. The 27 mer 3' primer incorporated an NcoI site and had the sequence CTT TAT GTA CA C CAT GGT GGA CAT GTT (SEQUENCE ID NO:7). The sequence of the 23 mer 5' kinesin primer was in part complementary to bases 114–127 and incorporated an EcoRI site. The sequence was ATG AAT TCC GGC GCC CCT AGC TG (SEQUENCE ID NO:8). The 185 bp PCR fragment was restricted with NcoI and EcoRI and ligated into EcoRI/NcoI, gel purified pCITE ECD TNFR. This plasmid has an 800 bp fragment encoding for the human p75 TNFR ECD. EcoRI/NcoI digestion removes the 592 bp IRES cite sequence (Novagen). The resultant plasmid was termed SR9.

The 970 bp SalI/EcoRI SR9 fragment containing the human kinesin HP and the human p75 TNF ECD was ligated in to SalI/EcoRI cut pBabe PAGO Neo to give plasmid SR10. pBabe PAGO Neo is a retroviral vector containing a BglII/PvuII, 1.7 kb fragment of HSV-TK downstream of the MuLv LTR followed by an SV40 early promoter and neomycin resistance gene. In SR10 the 5' hairpin kinesin UTR/p75TNFR ECD hybrid sequence from SR9 is inserted between the HSV-TK and SV40 early promoter sequence.

Thus, in SR10, this placed a 170 bp fragment encompassing the 5' kinesin UTR directly upstream of a reporter gene encoding the extracellular domain of the human p75 tumor necrosis factor receptor extracellular domain (p75 TNFR ECD) and directly downstream of a sequence encoding the thymidine kinase (TK) which is driven by a LTR MuLv promoter. Since the p75 TNFR reporter gene has no promoter, if expressed in transient transfection experiments, then it can be assumed that the hairpin structure acts as an IRES. The plasmid pBabe PAGO neo ECD which is identical except that the HP fragment is replaced by the known EMC IRES was used as a control. Quantities of p75 TNFR in cell supernatant was measured by ELISA (Bemelmans et al, 1993 J. Immunol. 150, 2007–2017), 2 days after transfection with varying quantities of either SR10 or pBabe Pago neo. The plasmid $PSV_2LUC$ (which codes for the luciferase reporter gene) was cotransfected with either test or control plasmid so that expression levels could be normalised for transfection efficiency. In addition, the arbitrary plasmid PUC 18 was included in all transfections to standardise the quantity of DNA transfected.

SR10 and pBabe PAGO neo ECD plasmids were transiently infected into COS cells. 10 μg of either of the latter plasmids was cotransfected with 5 μg of $PSV_2LUC$ and sufficient PUC18 plasmid to make the total quantity of transfected plasmid up to 25 μg. Transfections were transient and levels of recombinant protein production were measured 48 hours after transfection by ELISA based on 1:100 dilution of a monoclonal antibody 4C8 as a catching antibody and a second 1:5000 dilution of biotinylated polyclonal rabbit IgG anti-TNF-R75 antibody followed by streptavidine peroxidase. Quantities of luciferase in transfected cell protein extracts were determined and used to normalise expression values with respect to transfection efficiency. Antibodies for the ELISA were a gift from Dr M Bemelmans (Bemelmans et al, 1993 J. Immunol. 150 2007–2017.

The results showed that for the SR10 plasmid, recombinant p75 TNFR-ECD protein was produced at high levels confirming that the hairpin fragment does indeed act as an IRES. Levels of production appeared to be up to 10 times greater than those initiated by the EMC IRES of the pBabe PAGO neo plasmid when transfected in equal (10 μg) quantities.

I claim:

1. Isolated DNA from the portion of the β-chain of human kinesin genomic DNA lying between the 5'-end of the gene and the 3'-end of the first intron thereof, comprising nucleotides 430 to 474 of SEQ ID NO:1 or a variant thereof, wherein one to four nucleotides of said 430–474 nucleotides are varied or deleted.

2. DNA according to claim 1, which comprises nucleotides 430 to 551 of SEQ ID NO:1 or a said variant thereof.

3. DNA according to claim 2 which comprises, in addition to said nucleotides 430 to 551 or a said variant thereof, from 1 to 100 nucleotides of 5'- or 3'- flanking sequence of said β-chain of human kinesin genomic DNA.

4. DNA according to claim 1 which comprises, in addition to said nucleotides 430 to 474 or a said variant thereof, from 1 to 100 nucleotides of 5'- or 3'-flanking sequence of said β-chain of human kinesin genomic DNA.

5. Isolated DNA according to claim 1 which further comprises an open-reading frame from nucleotides 391–426 of SEQ ID NO:1 coding for protein of 12 amino acids.

6. A construct for expression of non-β-kinesin DNA encoding a protein, comprising in the order 5' to 3' (1) a eukaryotic promoter, (2) DNA according to claim 1 for enhancement of translation and (3) DNA coding for a protein other than β-kinesin.

7. A construct for expression of two protein coding DNAs which comprises in the order 5' to 3' (1) a eukaryotic promoter, (2) downstream of the promoter, DNA coding for a first protein other than β-kinesin and which lacks a transcription termination signal, (3) DNA according to claim 6 which serves both as an internal ribosome entry site (IRES) and a translational enhancer and (4) DNA coding for a second protein other than β-kinesin and which is distanced downstream from the IRES-translational enhancer DNA so as to permit translation of mRNA from the IRES.

8. A construct according to claim 6 wherein the promoter is one which is stronger than that of the native β-kinesin.

* * * * *

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
( A ) LENGTH: 838 base pairs
( B ) TYPE: nucleic acid
( C ) STRANDEDNESS: double
( D ) TOPOLOGY: linear ( i i ) MOLECULE TYPE: DNA (genomic)

( i i i ) SEQUENCE DESCRIPTION: SEQ ID NO: 1:

```
CCTGCCCCGA GAGCCCCACC CCCGTCCGCG TTACAACGG AAGGCCGCTG GGTCCTGCAC      60
CGTCACCCTC CTCCCTGTGA CCGCCCACCT GACACCCAAA CAACTTTCTC GCCCCTCCAG     120
TCCCCAGCTC GCCGAGCGCT TGCGGGGAGC CACCCAGCCT CAGTTTCCCC AGCCCCGGGC     180
GGGGCGAGGG GCGATGACGT CATGCCGGCG CGCGGCATTG TGGGCGGGG CGAGGCGGGG      240
CGCCGGGGGG AGCAACACTG AGACGCCATT TCGGCGGCCG GGACGGGCGC AAGGCGGCCG     300
AGCGGGACTG GCTGGGTCGG CTGGGCTGCT GGTGGAGGAG CCGCGGGGCT GTGCTCGGCG     360
GCCAAGGGGA CAGCGCGTGG GTGGCCGAGG ATGCTGCGGG GCGGTAGCTC CGGCGCCCCT     420
CGCTGGTGAC TGCTGCGCCG TGCCTCACAC AGCCGAGGCG GGCTCGGCGC ACAGTCGCTG     480
CTCCGCGCGC GCGCCCGGCG GCGCTCCAGG TGCTGACAGC GCGAGAGAGC GCGGCCCTCA     540
GGAGCAAGGC GGTGAGTCCC CGCGTCGTCG CCCCGGACCG CGGCCCCCTC CTCATCCTCC     600
GCCCCGTCCC TGTCCCGCTC CTCTTCGGAC CCGCCCCGGC CGCAACTCTG TCCCCATCCA     660
GGCCTCCTTC CCGGTTTGGT CCCGGCCCCT CTCCGTTCCC ACCCCGGTAC CCGCCCCAGT     720
TCACCGCCCC GGCCGGTCCG CGACCCCTTC TAGGTTCAGG TCGGGTTCTT GTCCCCGGCC     780
CTTTTGCCAG CCCCGGCTCC CGGCGCCGCG CGTCCTCCCC ATCCGCGTCC CACTGCAG      838
```

( 2 ) INFORMATION FOR SEQ ID NO: 2:

( i ) SEQUENCE CHARACTERISTICS:
( A ) LENGTH: 60 base pairs
( B ) TYPE: nucleic acid
( C ) STRANDEDNESS: double
( D ) TOPOLOGY: linear ( i i ) MOLECULE TYPE: DNA (genomic)

( i i i ) SEQUENCE DESCRIPTION: SEQ ID NO: 2:

```
GGGTGGCCGA GG ATG CTG CGG GGC GGT AGC TCC GGC GCC CCT CGC TGG       48
              Met Leu Arg Gly Gly Ser Ser Gly Ala Pro Arg Trp
              1                5                    10

TGACTGCTGC GC                                                       60
```

( 2 ) INFORMATION FOR SEQ ID NO: 3:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( i i i ) SEQUENCE DESCRIPTION: SEQ ID NO: 3:

```
Met Leu Arg Gly Gly Ser Ser Gly Ala Pro Arg Trp
1                5                    10
```

( 2 ) INFORMATION FOR SEQ ID NO: 4:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) SEQUENCE DESCRIPTION: SEQ ID NO: 4:

```
GTCGGGGTGA GG ATG CTG CGG GGC GGC TGC GGA GGC GTC GCT TGC TGC       48
              Met Leu Arg Gly Gly Cys Gly Gly Val Ala Cys Cys
              1                5                    10

TGAGGCGGCT GG                                                       60
```

( 2 ) INFORMATION FOR SEQ ID NO: 5:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( i i i ) SEQUENCE DESCRIPTION: SEQ ID NO: 5:

```
Met Leu Arg Gly Gly Cys Gly Gly Val Ala Cys Cys
1                5                    10
```

( 2 ) INFORMATION FOR SEQ ID NO: 6:

( i ) SEQUENCE CHARACTERISTICS:
        ( A ) LENGTH: 123 base pairs
        ( B ) TYPE: nucleic acid
        ( C ) STRANDEDNESS: single
        ( D ) TOPOLOGY: linear ( i i ) MOLECULE TYPE: mRNA ( i i i ) SEQUENCE DESCRIPTION: SEQ ID NO: 6:

```
CUGCUGCGCC GUGCCUCACA CAGCCGAGGC GGGCUCGGCG CACAGUCGCU GCUCCGCGCG      60
CGCGCCGCGC GGCGCUCCAG GUGCUGACAG CGCGAGAGAG CGCGGCCCUC AGGAGCAAGG     120
CGA                                                                  123
```

( 2 ) INFORMATION FOR SEQ ID NO: 7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) SEQUENCE DESCRIPTION: SEQ ID NO: 7:

CTTTATGTAC ACCATGGTGG ACATGTT    27

( 2 ) INFORMATION FOR SEQ ID NO: 8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) SEQUENCE DESCRIPTION: SEQ ID NO: 8:

ATGAATTCCG GCGCCCTAG CTG    23